(12) United States Patent
Ikeuchi et al.

(10) Patent No.: US 11,925,540 B2
(45) Date of Patent: Mar. 12, 2024

(54) ELASTIC SHEET FOR ABSORBENT ARTICLE AND ABSORBENT ARTICLE

(71) Applicant: Unicharm Corporation, Ehime (JP)

(72) Inventors: Norihito Ikeuchi, Kagawa (JP); Satoshi Mitsuno, Kagawa (JP)

(73) Assignee: Unicharm Corporation, Ehime (JP)

( * ) Notice: Subject to any disclaimer, the term of this patent is extended or adjusted under 35 U.S.C. 154(b) by 1007 days.

(21) Appl. No.: 16/845,450

(22) Filed: Apr. 10, 2020

(65) Prior Publication Data

US 2020/0237577 A1 Jul. 30, 2020

Related U.S. Application Data

(63) Continuation of application No. PCT/JP2018/023397, filed on Jun. 20, 2018.

(30) Foreign Application Priority Data

Oct. 12, 2017 (JP) .................................. 2017-198788

(51) Int. Cl.
*B32B 3/22* (2006.01)
*A61F 13/49* (2006.01)
(Continued)

(52) U.S. Cl.
CPC .... *A61F 13/49012* (2013.01); *A61F 13/4902* (2013.01); *A61F 13/4942* (2013.01); (Continued)

(58) Field of Classification Search
None
See application file for complete search history.

(56) References Cited

U.S. PATENT DOCUMENTS 6,204,210 B1 3/2001 Koczab
2002/0045877 A1* 4/2002 Shimada ........... A61F 13/49011
604/385.29
(Continued)

FOREIGN PATENT DOCUMENTS

EP 589222 A2 3/1994
JP H06-190998 A 7/1994
(Continued)

OTHER PUBLICATIONS

Machine Translation of JP-2008142342-A, Jun. 2008 (Year: 2008).*
(Continued)

*Primary Examiner* — Jeffrey A Vonch
(74) *Attorney, Agent, or Firm* — Osha Bergman Watanabe & Burton LLP

(57) ABSTRACT

An elastic sheet for an absorbent article includes a first fibrous layer disposed on a first surface of the elastic sheet, a second fibrous layer disposed on a second surface of the elastic sheet opposite to the first surface, and contractible elastic members secured between the first fibrous layer and the second fibrous layer. The first fibrous layer and the second fibrous layer each include continuous fibers of thermoplastic and gathers formed between adjacent ones of the elastic members. The gathers are disposed in an intersecting direction intersecting with a direction in which the elastic members extend. An average flexural rigidity value of the first fibrous layer and the second fibrous layer in accordance with a KES method is $0.0035 \times 10^{-4}$ to $0.022 \times 10^{-4}$ (N·m²/m). A thickness under a compression load to the gathers in accordance with the KES method is 0.22 to 1.5 mm.

20 Claims, 4 Drawing Sheets

(51) Int. Cl.

| | | |
|---|---|---|
| *A61F 13/494* | (2006.01) | |
| *B32B 3/18* | (2006.01) | |
| *B32B 3/28* | (2006.01) | |
| *B32B 5/02* | (2006.01) | |
| *B32B 5/04* | (2006.01) | |
| *B32B 5/26* | (2006.01) | |
| *B32B 7/14* | (2006.01) | |
| *B32B 27/02* | (2006.01) | |
| *A61F 13/15* | (2006.01) | |
| *B32B 7/022* | (2019.01) | |
| *B32B 27/32* | (2006.01) | |

(52) U.S. Cl.
 CPC .................. *B32B 3/18* (2013.01); *B32B 3/22* (2013.01); *B32B 3/28* (2013.01); *B32B 5/022* (2013.01); *B32B 5/04* (2013.01); *B32B 5/26* (2013.01); *B32B 5/266* (2021.05); *B32B 5/267* (2021.05); *B32B 5/269* (2021.05); *B32B 5/271* (2021.05); *B32B 7/14* (2013.01); *B32B 27/02* (2013.01); *A61F 2013/15959* (2013.01); *A61F 2013/15967* (2013.01); *A61F 2013/15991* (2013.01); *A61F 2013/49022* (2013.01); *A61F 2013/49023* (2013.01); *A61F 2013/49025* (2013.01); *A61F 2013/49031* (2013.01); *A61F 2013/49098* (2013.01); *A61F 2013/4948* (2013.01); *B32B 7/022* (2019.01); *B32B 27/32* (2013.01); *B32B 2250/03* (2013.01); *B32B 2250/20* (2013.01); *B32B 2250/24* (2013.01); *B32B 2250/40* (2013.01); *B32B 2262/02* (2013.01); *B32B 2262/0207* (2013.01); *B32B 2262/0253* (2013.01); *B32B 2262/0292* (2013.01); *B32B 2305/10* (2013.01); *B32B 2305/20* (2013.01); *B32B 2307/51* (2013.01); *B32B 2307/546* (2013.01); *B32B 2307/718* (2013.01); *B32B 2307/72* (2013.01); *B32B 2307/732* (2013.01); *B32B 2555/02* (2013.01); *Y10T 428/24669* (2015.01); *Y10T 428/24686* (2015.01); *Y10T 428/24694* (2015.01); *Y10T 428/24702* (2015.01); *Y10T 428/24711* (2015.01); *Y10T 428/24851* (2015.01); *Y10T 428/24942* (2015.01); *Y10T 442/659* (2015.04); *Y10T 442/66* (2015.04); *Y10T 442/68* (2015.04); *Y10T 442/681* (2015.04)

(56) References Cited

U.S. PATENT DOCUMENTS

| | | | |
|---|---|---|---|
| 2004/0219854 A1 | 11/2004 | Groitzsch et al. | |
| 2006/0025746 A1* | 2/2006 | Sasaki | A61F 13/49466 604/385.24 |
| 2008/0000003 A1* | 1/2008 | Melander | B32B 25/04 2/69 |
| 2009/0035527 A1* | 2/2009 | Kobayashi | D04H 1/593 428/167 |
| 2009/0275909 A1* | 11/2009 | Sakaguchi | A61F 13/4902 428/182 |
| 2009/0306616 A1* | 12/2009 | Wennerback | A61F 13/51121 604/378 |
| 2010/0076394 A1* | 3/2010 | Hayase | A61F 13/49019 604/385.29 |
| 2011/0118690 A1 | 5/2011 | Oku et al. | |
| 2011/0137275 A1 | 6/2011 | Oku et al. | |
| 2011/0184368 A1 | 7/2011 | Oku et al. | |
| 2012/0029460 A1* | 2/2012 | Yamashita | A61F 13/49017 604/385.26 |
| 2012/0165774 A1 | 6/2012 | Otsubo et al. | |
| 2014/0378934 A1* | 12/2014 | Takahashi | A61F 13/49011 604/385.26 |
| 2015/0126955 A1* | 5/2015 | Sauer | A61F 13/49011 604/385.29 |
| 2015/0126956 A1* | 5/2015 | Raycheck | A61F 13/5638 604/385.29 |
| 2015/0140278 A1* | 5/2015 | Okuda | B32B 5/26 428/174 |
| 2015/0230995 A1* | 8/2015 | Kaneko | A61F 13/49011 604/385.3 |
| 2015/0305948 A1* | 10/2015 | Sakaguchi | A61F 13/51466 604/385.04 |
| 2015/0320612 A1* | 11/2015 | Seitz | A61F 13/55105 604/385.01 |
| 2015/0328056 A1* | 11/2015 | Een | A61F 13/15707 442/329 |
| 2016/0067115 A1* | 3/2016 | Ishikawa | A61F 13/496 156/60 |
| 2016/0206481 A1* | 7/2016 | Adachi | A61F 13/4902 |
| 2016/0250082 A1* | 9/2016 | Hamamoto | A41B 9/00 2/400 |
| 2017/0056257 A1* | 3/2017 | Nishikawa | A61F 13/496 |
| 2017/0143560 A1* | 5/2017 | Morimoto | A61F 13/49011 |
| 2018/0042788 A1* | 2/2018 | Kurohara | A61F 13/49 |
| 2018/0221219 A1* | 8/2018 | Morimoto | A61F 13/496 |
| 2019/0076302 A1* | 3/2019 | Yamada | D21H 27/32 |
| 2019/0374399 A1* | 12/2019 | Morimoto | A61F 13/15699 |
| 2019/0374400 A1* | 12/2019 | Morimoto | A61F 13/49015 |
| 2019/0374401 A1* | 12/2019 | Seitz | A61F 13/49011 |
| 2019/0374402 A1* | 12/2019 | Morimoto | A61F 13/49012 |
| 2019/0374403 A1* | 12/2019 | Wang | A61F 13/84 |
| 2021/0137750 A1* | 5/2021 | Ishikawa | A61F 13/496 |

FOREIGN PATENT DOCUMENTS

| | | | | |
|---|---|---|---|---|
| JP | 2001-503336 A | | 3/2001 | |
| JP | 2001252303 A | * | 9/2001 | |
| JP | 2004-330777 A | | 11/2004 | |
| JP | 2007-117117 A | | 5/2007 | |
| JP | 2008142342 A | * | 6/2008 | ....... A61F 13/15593 |
| JP | 2009-106468 A | | 5/2009 | |
| JP | 2011-067602 A | | 4/2011 | |
| JP | 2016-013687 A | | 1/2016 | |
| JP | 2016013687 A | * | 1/2016 | |
| WO | 2009/104673 A1 | | 8/2009 | |

OTHER PUBLICATIONS

International Search Report issued in corresponding International Application No. PCT/JP2018/023397 dated Sep. 25, 2018 (5 pages).
Written Opinion of the International Searching Authority issued in corresponding International Application No. PCT/JP2018/023397 dated Sep. 25, 2018 (3 pages).
International Preliminary Report on Patentability issued in corresponding International Application No. PCT/JP2018/023397 dated Apr. 14, 2020 (6 pages).

* cited by examiner

ELASTIC SHEET FOR ABSORBENT ARTICLE AND ABSORBENT ARTICLE

CROSS-REFERENCE TO RELATED APPLICATIONS

This application is based on and claims priority under 35 U.S.C. § 119 to Japanese Patent Application No. 2017-198788 filed on Oct. 12, 2017, the contents of which are incorporated herein by reference.

BACKGROUND

Technical Field

The present invention generally relates to an elastic sheet for an absorbent article such as a disposable diaper and a menstruation napkin/pad and an absorbent article for using the same.

Related Art

Conventional elastic sheets for absorbent articles include a first fibrous layer, a second fibrous layer, and a plurality of elastic members secured between the first and second fibrous layers in a contractible manner under tension (see Patent Literature 1). The first fibrous layer and the second fibrous layer are bonded to each other with adhesive applied to the entire periphery of the plurality of elastic members.

Patent Literature 1: Japanese Patent Application Publication No. 2016-13687

According to the elastic sheet disclosed in Patent Literature 1, provided is good fittability to a wearer's skin and relatively thin as a whole and excellent in flexibility, and can give a good feeling to the wearer's skin when the elastic sheet is disposed to a skin facing surface of the absorbent articles, by appropriately controlling a rigidity of a fibrous nonwoven fabric constructing the first and second fibrous layers, a pitch of the elastic members and an amount of adhesive coated to the entire periphery of the elastic members.

Although such an elastic sheet provides the outside appearance having excellent aesthetics by approximately equal formation of gathers having a thickness of 0.5 to 10 mm over the entire surface of the elastic sheet, gather marks may be left on a wearer's skin due to a bite thereinto of the gathers. When the pitch of the elastic members is made large to suppress the bite into the wearer's skin, the fittability of the elastic sheet to the wearer's skin may be degraded, and when decreasing an amount of adhesive to be applied to the entire peripheral of the elastic members to reduce the rigidity of the fibrous nonwoven fabric, the elastic members secured to the elastic sheet may be released therefrom while the absorbent article is worn.

SUMMARY

One or more embodiments provide an elastic sheet for an absorbent article and an absorbent article using the elastic sheet that has good fittability to a wearer's skin and can suppress the gather marks from being left on the wearer's skin.

One or more embodiments of the present invention are directed to an elastic sheet for an absorbent article having a first surface and a second surface opposite to the first surface, and including a first fibrous layer located on the first surface and a second fibrous layer located on the second surface respectively constructed of continuous fibers of thermoplastic resin; a plurality of elastic members being secured between the first fibrous layer and the second fibrous layer in a contractible manner; the first fibrous layer and the second fibrous layer respectively having a plurality of gathers formed between the elastic members adjacent to each other in a direction intersecting with a direction in which the elastic members extend; and each average flexural rigidity value of the first fibrous layer and the second fibrous layer in accordance with a Kawabata Evaluation System (KES) method being $0.0035 \times 10^{-4}$ to $0.022 \times 10^{-4}$ (N·m²/m), and a thickness under a compression load to the gathers in accordance with the KES method being 0.22 to 1.5 mm.

According to one or more embodiments, in the elastic sheet for the absorbent article, a compression workload under a compression load to the gathers in accordance with the KES method is 0.236 to 5.0 N·m/m², and a compression resilience rate in accordance with the KES method is 19 to 36%.

In such an elastic sheet for the absorbent article, the compression workload WC and the compression resilience rate RC are a relative low numerical value, the convex parts are easily compressed by an external force, and a shape resilience after compressed is low. Thus, the convex parts are easily compressed when being in contact with the wearer's skin, a repulsive force against the wearer's is low due to the low resilience after compressed, and the gather marks can be suppressed from being left on the wearer's skin with the dispersion of a contact pressure.

According to one or more embodiments, in the elastic sheet for the absorbent article, the first fibrous layer is formed of a spun-melt fibrous nonwoven fabric constructed of polyethylene fibers and the second fibrous layer is formed of a spun-melt fibrous nonwoven fabric including at least partly polyolefin fibers.

In such an elastic sheet for the absorbent article, the first fibrous layer is low in rigidity and excellent in flexibility compared to those of the second fibrous layer, and thus the gathers formed on the skin facing surface have gently raised shapes compared to those of the non-skin facing surface, and a contact pressure against the wearer's skin is dispersed when the article is worn, the gather mark can be suppressed from being left on the wearer's skin.

According to one or more embodiments, in the elastic sheet for the absorbent article, the first fibrous layer and the second fibrous layer are formed of a spun-melt fibrous nonwoven fabric constructed of polyethylene fibers.

In such an elastic sheet for the absorbent article, both the first fibrous layer and the second fibrous layer have good flexibility, and thus the gathers having relatively small concave and convex parts are formed, and the gather marks can be further suppressed from being on the wearer's skin.

According to one or more embodiments, in the elastic sheet for the absorbent article, the first fibrous layer and the second fibrous layer respectively have a plurality of fusion parts of the continuous fibers, and a rigidity difference between the fused parts and non-fusion parts in the second fibrous layer is larger than a rigidity difference between the fused parts and the non-fusion parts in the first fibrous layer.

In such an elastic sheet for the absorbent article, the first fibrous layer is more excellent than the second fibrous layer in flexibility as a whole, and is repeated with small ups and downs by the contractile force of a plurality of elastic members. Thus, the gathers on the skin facing surface are smaller than the gathers on the non-skin facing surface in thickness, and the gathers mark can be suppressed from being left on the wearer's skin.

According to one or more embodiments, in the elastic sheet for the absorbent article, each mass of the first fibrous layer and the second fibrous layer is 10 to 30 g/m², each apparent density of the first fibrous layer and the second fibrous layer is 0.04 to 0.15 g/cm³, and a pitch between the plurality of elastic members arranged in the intersecting direction is 2.0 to 12.0 mm.

According to one or more embodiments, in the elastic sheet for the absorbent article, a fineness of the polyethylene fibers is 1.5 to 4.0 dtex, and a fineness of the polypropylene fibers is 0.9 to 2.5 dtex.

According to one or more embodiments, in the elastic sheet for the absorbent article, the elastic sheet has a skin facing surface and a non-skin facing surface opposite thereto, the first surface corresponds to the skin facing surface, and the second surface corresponds to the non-skin facing surface.

One or more embodiments is directed to an absorbent article using the elastic sheet.

According to one or more embodiments, in the absorbent article, the absorbent article is a disposable diaper having a front waist region, a rear waist region and a crotch region, and at least one of a waist elastic sheet defining the front waist region and the rear waist region, a leg elastic sheet disposed along a leg opening edge in the crotch region, and a leakage barrier flap extending from the crotch region to the front and rear waist regions is formed of the elastic sheet.

The elastic sheet for the absorbent article according to one or more embodiments has good fittability to the wearer's skin under the contractile force of the elastic members, each average flexural rigidity value of the first and second fibrous layers in accordance with the KES method is $0.0035 \times 10^{-4}$ to $0.022 \times 10^{-4}$ (N·m²/m), and a thickness under a compression load of the gathers in accordance with the KES method is 0.22 to 1.5 mm. Thus, the elastic sheet has excellent flexibility, and the gather marks can be suppressed from being left on the wearer's skin. In particular, it is beneficial to put into practical use as the elastic sheet for an article such as a disposable diaper and a menstruation pad/napkin and as a disposable diaper and a menstruation pad/napkin using the sheet.

DETAILED DESCRIPTION

Figure 1:
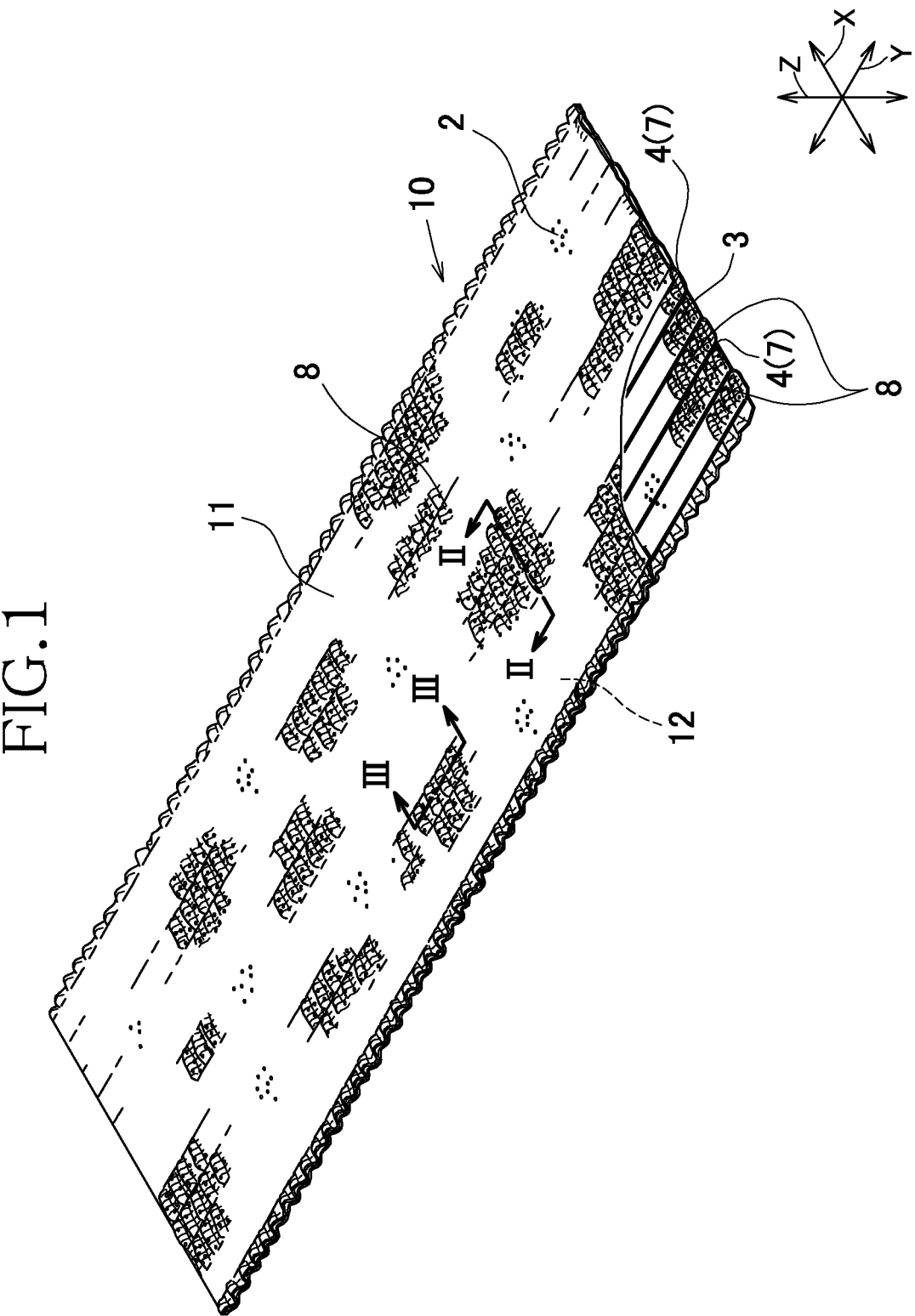
FIG. 1 is a perspective view illustrating one example of an elastic sheet for an absorbent article according to one or more embodiments.
Figure 2:
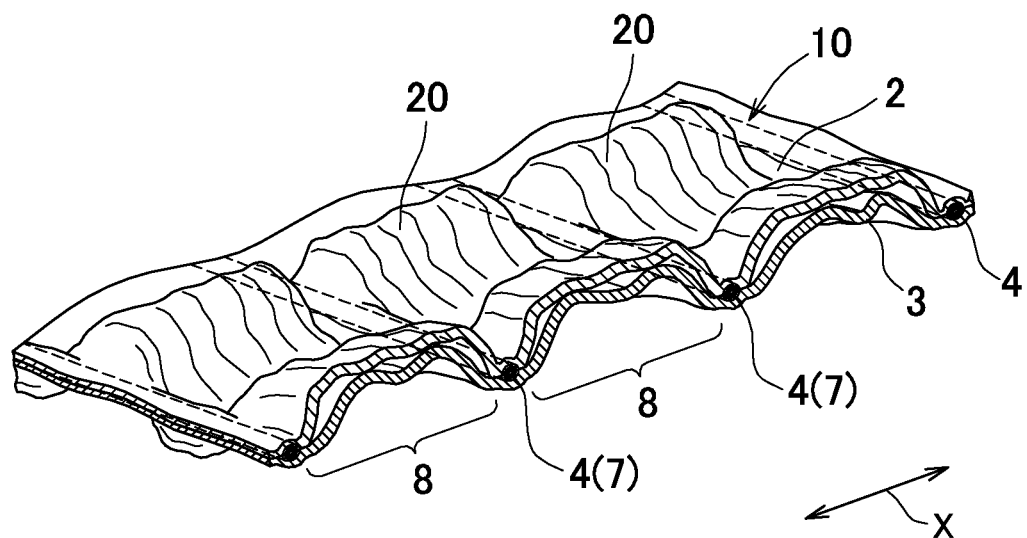
FIG. 2 is a cross-sectional perspective view taken along II-II line of the elastic sheet in FIG. 1.
Figure 3:
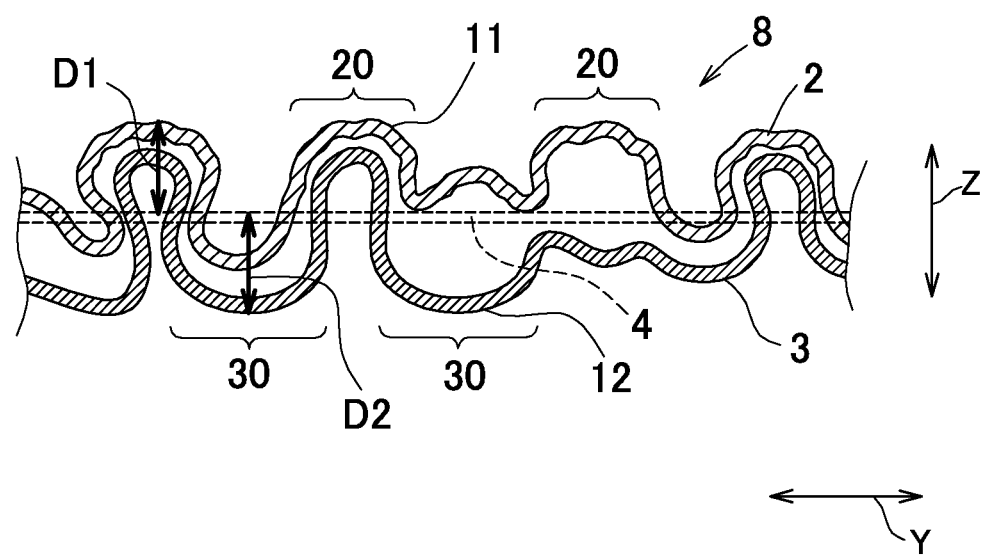
FIG. 3 is a cross-sectional end view taken along III-III line in FIG. 1.

Referring to FIGS. 1 to 3, an elastic sheet 10 for an absorbent article according to one or more embodiments has a first direction Y, a second direction X intersecting with the first direction Y, a thickness direction Z intersecting with the first and second directions Y, X, and include a first surface 11, a second surface 12 opposite to the first surface 11, a first fibrous layer 2 located on the first surface 11, a second fibrous layer 3 located on the second surface 12, and a plurality of elastic members 4 arranged in parallel to the first direction Y in a contractible manner under tension between the first and second layers 2, 3. The first surface 11 and the second surface 12 of the elastic sheet 10 respectively correspond to a skin facing surface and a non-skin facing surface of the absorbent article. The elastic members 4 may be secured between the first and second fibrous layers 2, 3 with hot melt adhesive (not shown) applied to each of the entire periphery of the elastic members. The first and second fibrous layers 2, 3 are integrally joined to each other with the hot melt adhesive. The absorbent article according to one or more embodiments includes disposable diapers, menstruation napkins, in addition, various well-known articles such as panty liners and incontinence pads for absorbing and containing body exudates, for example, such as menstrual blood, urine or feces. The elastic sheet 10 may be used as sheet materials coming in contact with the wearer's skin in the absorbent article, for example, may suitably be used as sheet materials including waist sheets to form waist panels, leakage barrier sheets extending in the longitudinal direction along both sides of an absorbent body, and leg elastic sheets to form leg elastic members disposed along leg opening edges.

The first and second fibrous layers 2, 3 of the elastic sheet 10 is formed of fibrous nonwoven fabrics constructed of continuous fibers of thermoplastic resin. As the fibrous nonwoven fabrics constructing the first and second fibrous layers 2, 3, spun-melt fibrous nonwoven fabrics, especially, spun-bonded fibrous nonwoven fabrics, spun-bonded/melt-blown/spun-bonded fibrous nonwoven fabrics (SMS) are suitably used. As the continuous fibers constructing these fibrous nonwoven fabrics, various well-known synthetic fibers, for example polyolefin fibers including polypropylene(PP) and polyethylene(PE) are suitably used. In one or more embodiments, as the first fibrous layer 2, spun-bonded fibrous fibers including polyethylene fibers having a fineness of 1.5 to 4.0 dtex, and as the second fibrous layer 3, spun-bonded fibrous fibers including polypropylene fibers having a fineness of 0.9 to 2.5 dtex are used. In particular, the first fibrous layer 2 is composed of polyethylene fibers softer than polypropylene fibers and thereby is low in rigidity and excellent in flexibility compared to the second fibrous layer 3. In order that the first fibrous layer 2 may be low in rigidity and high in flexibility compared to the second fibrous layer 3, it depends on a rigidity difference between the fibers constructing both the layers 2, 3, in addition it can be adjusted appropriately, at least by an increase and decrease of mass or density of fibrous nonwoven fabrics.

Use of the spun-bonded fibrous nonwoven fabrics or the SMS fibrous nonwoven fabrics constructed of the continuous fibers as the first fibrous layer 2 located on the first surface 11 makes it possible to give to the wearer an excellent texture and a smooth feeling with no fluff on surfaces compared to other short synthetic fibers. The spun-boned fibrous nonwoven fabrics are also easy to control fiber orientation compared to other fibrous nonwoven fabrics. Thus, for example, when staple (short) fibrous nonwoven fabrics are used as at least one of the first and second fibrous layers 2, 3, they are excellent in flexibility and elasticity but inferior in tensile strength, while the use of the spun-bonded fibrous nonwoven fabrics constructed of the continuous fibers as both the first and second fibrous layers 2, 3 makes it possible to obtain a well-balanced composite elastic sheet having desired tensile strength and elasticity.

At the time when the elastic sheet 10 has been stretched, a mass of the elastic sheet 10 is for example 25 to 135 g/m$^2$ and may be 40 to 80 g/m$^2$, and a mass of the first and second fibrous layer 2, 3 respectively are for example 10 to 30 g/m$^2$ and may be 12 to 25 g/m$^2$. When the mass of the elastic sheet 10 is less than 25 g/m$^2$, the elastic sheet 10 is excellent in flexibility but makes it difficult to have sufficient tensile strength. When the mass of the elastic sheet 10 is more than 135 g/m$^2$, the elastic sheet 10 is possible to have relatively high tensile strength but impossible to have sufficient flexibility, and thereby impossible to deform along the wearer's body or to give good fittability to the wearer's skin.

Each thickness of the first and second fibrous layers 2, 3 under 2.942 hpa load is 0.10 to 0.60 mm, each apparent density of the first and second fibrous layers 2, 3 is 0.04 to 0.15 g/cm$^3$, and may be 0.09 to 0.12 g/cm$^3$. When the apparent density is less than 0.04 g/cm$^3$, the first and second fibrous layers 2, 3 may easily fluff because the fusion parts are less. When the apparent density is more than 0.15 g/cm$^3$, the rigidity of the elastic sheet 10 is relatively high, and particularly the elastic sheet 10 may create a rigid feeling against the wearer's skin when the elastic sheet 10 is used at parts coming in contact with a weak skin part of the wearer such as the groins in the absorbent article.

The mass of each fibrous nonwoven fabric was measured in accordance with a JIS L 1096 method. The apparent density was determined from an average value (N=3) calculated by the mass and the thickness obtained by the measurements.

A plurality of elastic members 4 are thread-like, string-like or strand-like elastic materials arranged approximately in parallel in the first direction Y and at intervals in the second direction X. The elastic members 4 are secured between the first and second fibrous layers 2, 3 in a state stretched by for example 1.5 to 3.0 times, and may be by 2.2 to 2.7 times, from their natural states.

The elastic materials may include without limitation various well-known synthetic rubber such as styrene rubber, urethane rubber, ester rubber, polyurethane rubber and polyethylene rubber, in addition to natural rubber. The fineness of the elastic members 4 are, but not limited in particular, 200 to 1100 dtex, and may be 300 to 1000 dtex. When the fineness is less than 200 dtex, the elastic sheet 10 may not exert the required elasticity in a state that shapes and sizes of the gathers formed by a pitch between the elastic members 4 has been controlled. When the fineness is more than 1100 dtex, the elastic members 4 is likely to be seen from outside through the second fibrous layer 3 located on the non-skin facing surface of the absorbent article. In such case, when the elastic sheet 10 is used as a sheet material forming the outer surface of the absorbent article in particular, the absorbent article may be recognized at a glance to be provided with a plurality of elastic members, which is undesirable in appearance.

The pitch of the elastic members is not particularly limited because of being appropriately adjustable to control cross-sectional shapes and sizes including lengths of the gathers formed on the elastic sheet 10, but is for example 2.0 to 12.0 mm, and may be 4.0 to 10.0 mm, to suppress the bite of the gathers into the wearer's skin. As used herein, the term "pitch" means a distance between centers of the elastic members 4 adjacent to each other in the second direction X.

In the present embodiment, the first and second fibrous layers 2, 3 are joined to each other with adhesive applied continuously or partially to the entire periphery of each of the elastic members 4. Thus, the pitch between the elastic members 4 corresponds to the pitch between adjacent lines joining the first and second fibrous layers 2, 3 to each other. The first and second fibrous layers 2, 3 joined only by the adhesive applied to the entire periphery of each of the elastic members 4 makes the elastic sheet 10 relatively flexible and a texture to a wearer's skin improvable with the flexibility of the first fibrous layer 2.

The first and second fibrous layers 2, 3 may be joined to each other with adhesive applied in known various pattern to a facing surface of at least one of the first and second fibrous layers 2, 3 rather than the adhesive applied to the entire periphery of each of the elastic members 4. However, in that case, it is necessary to appropriately adjust an adhesive applying amount so as not to suppress the elasticity of the elastic members 4. In the case where the first and second fibrous layers 2, 3 are joined by a plurality of adhesive lines, the adhesive lines may extend in an extending direction of the elastic members 4 or in an intersecting direction with the extending direction of the elastic members 4. To join the first and second fibrous layers 2, 3, various well-known adhesives may be used without limitation, but in order that the elasticity of the elastic sheet 10 is not suppressed as much as possible, rubber-based hot melt adhesive such as styrene-butadiene-styrene based or styrene-isoprene-styrene based hot melt adhesive may be used.

Referring to FIGS. 1 to 3, the elastic sheet 10 includes joining areas 7 in which the first and second fibrous layers 2, 3 are joined to each other with hot melt adhesive applied to the entire periphery of each of the elastic members 4, and non-joining areas 8 in which the first and second fibrous layers 2, 3 are not joined to each other with hot melt adhesive located between the elastic members 4 adjacent to each other in the second direction X. The non-joining areas 8 of the elastic sheet 10 in a non-stretched state have a gather-like concavity and convexity repeated, and include a plurality of convex parts 20 located onto the side of the skin facing surface bordering the elastic members 4 and a plurality of concave parts 30 located onto the side of the non-skin facing surface bordering the elastic members 4. The concave parts 30 of the non-joining areas 8 are convex parts when viewed from the non-skin facing surface. The second surface 12, similar to the first surface 11, has a structure of concavity and convexity with the concave parts 30. As used herein, the term "gathers" of the elastic sheet 10 means the gathers formed by the entire ups and downs of the first and second fibrous layers 2, 3, and the term "thickness" of the gathers means a dimension in the thickness direction between a top edge of each convex part 20 and a bottom edge of each concave part 30 (both including thickness of the first and second fibrous layers 2, 3). Such a "thickness" of the gathers is different depending on each gather and does not mean a thickness itself of the elastic sheet 10.

Since the first fibrous layer 2 is low in rigidity and excellent in flexibility compared to the second fibrous layer 3, the first fibrous layer 2 repeats narrower tops and downs than those of the second fibrous layer 3 in a state that the elastic sheet 10 has the convex part 20 and the concave part 30 alternately located in the second direction X under the contractile force of the elastic members 4. In this way, the first fibrous layer 2 has a configuration repeating the narrower tops and downs than those of the second fibrous layer 3, and thereby the convex parts 20 protrude gently like collapsing outward in the thickness direction Z without protruding higher outward in the thickness direction Z than the concave part 30, and an apparent thickness (height) D1 of the convex parts 20 is smaller than an apparent thickness D2 of the concave parts 30. As used herein, the term "apparent thickness D1" of the convex parts 20 means a dimension in the thickness direction Z between the elastic members 4 and the top edges of the convex part 20, and the term "apparent thickness D2" of the concave parts 30 means a dimension in the thickness direction Z between the elastic members 4 and the bottom edges of the concave parts 30.

According to one or more embodiments, in the case where the first and second fibrous layers 2, 3 are constructed of spun-bonded fibrous nonwoven fabrics using continuous fibers, each fibrous layer has thermal fusion parts at contact parts of the continuous fibers. At the fusion parts, each constructional fiber does not maintain a fiber shape due to the thermal fusion with a part formed into a film-like state and is higher in rigidity than non-fusion parts. Also, in the first and second fibrous layers 2, 3, the fusion parts have high rigidity compared to the non-fusion parts. However, the constructional fibers (polyolefin, polyethylene fibers) of the first fibrous layer 2 are more flexible than constructional fibers (polyolefin, polypropylene fibers) of the second fibrous layer 3, the fineness of the former constructional fibers is larger than the fineness of the latter constructional fibers, and the number of the former containing fibers is less than the number of the latter containing fibers in substantially the same mass of the sheet, and thus the rigidity difference between the fusion parts and the non-fusion parts of the first fibrous layer 2 is relatively small and is smaller than the rigidity difference between the fusion parts and non-fusion parts of the second fibrous layer. This makes the first fibrous layer 2 more flexible as a whole. It is considered that such sheet properties affect the difference between the thickness D1 and the thickness D2.

In view of the above, the first surface 11 is excellent in smoothness and has a larger area contacting with the wearer's skin compared to the second surface 12. Thus, the contact pressure of the elastic sheet 10 against the wearer's skin under the contractile force of the elastic members 4 is more dispersed compared to the case where the elastic sheet 10 partially comes in contact with the wearer's skin, and the gather marks are likely to be left. As used herein, the term "gather marks" means the pressure marks left on the wearer's skin due to the convex parts 20 of the elastic sheet 10, and the term "rubber elasticity marks" means the pressure marks left on the wearer's skin due to the elastic members 4.

Each average value of the flexural rigidity value B1 of the first fibrous layer 2 and the flexural rigidity value B2 of the second fibrous layer is for example $0.0035 \times 10^{-4}$ to $0.022 \times 10^{-4}$ (N·m²/m). In the case where each average value of the flexural rigidity value B1, B2 is less than $0.0035 \times 10^{-4}$ (N·m²/m), the tensile strength of the elastic sheet 10 is low, and a part of the absorbent article may be broken during wearing. In the case where each average value of the flexural rigidity value B1, B2 is more than $0.022 \times 10^{-4}$ (N·m²/m), the rigidity of the sheet is high, and the elastic sheet 10 is difficult to conform to the wearer's body shape and the fittability to the wearer's body may be low.

<Measurement Method for Flexural Rigidity Value>

The measurement for the flexural rigidity value B1 of the first fibrous layer 2 and the flexural rigidity value B2 of the second fibrous layer 3 were measured by KES-FB2-AUTO-A FLEXURAL MEASURING AND TEST MACHINE of KATO TECH CO, LTD in Japan. First, about each of the first and second fibrous layers 2, 3, the required areas of fibrous nonwoven fabrics forming them were cut by 10 cm×10 cm to obtain each test piece. Next, each test piece was fixed between chucks of the measuring test machine so as to measure in the first direction Y of the elastic sheet. Each test piece was bent onto the front side up to the maximum curvature+2.5 cm$^{-1}$ and each bent test piece was undone after bent onto the back side up to the maximum curvature $-2.5$ cm$^{-1}$. The flexural rigidity values B1, B2 [×10$^{-4}$ (N·m²/m)] were calculated from the average value of an inclination of each test piece at the time when the slope of a bending moment for the first time curvature bending on the front side was almost constant and the slope of each test piece at the time when the slope of a bending moment for the first time curvature bending onto the back side was almost constant. Each test piece was measured by N=5, and the results were calculated by averaging.

Each average value of the flexural rigidity value B1 of the first fibrous layer 2 and the flexural rigidity value B2 of the second fibrous layer 3 was calculated by the following formula. {(the flexural rigidity value B1 of the first fibrous layer 2×the mass of the first fibrous layer 2)/(the mass of first fibrous layer 2+the mass of the second fibrous layer 3)}+{(the flexural rigidity value B2 of the second fibrous layer 3×the mass of the second fibrous layer 3)/(the mass of the first fibrous layer 2+the mass of the second fibrous layer 3)}

Figure 4:
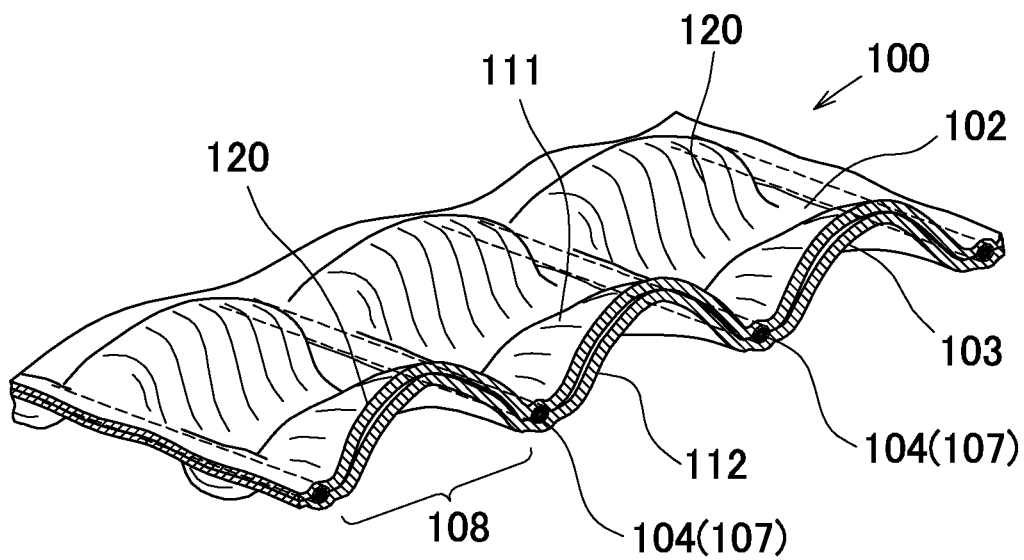
FIG. 4 is a cross-sectional perspective view of a conventional elastic sheet similar to FIG. 2.
Figure 5:
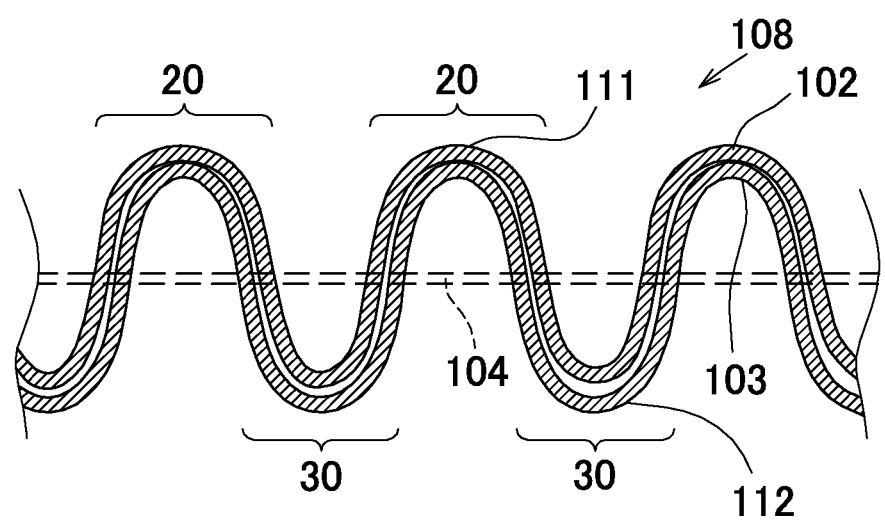
FIG. 5 is a cross-sectional end view of the conventional elastic sheet similar to FIG. 3.

Referring to FIGS. 4 and 5, a conventional elastic sheet 100 has a first surface 111, a second surface 112 opposite thereto, a first fibrous layer 102 located on the first surface 111, a second fibrous layer 103 located on the second surface 112, and a plurality of elastic members 104 secured with adhesive between the first fibrous layer 102 and the second fibrous layer 103. The first fibrous layer 102 and the second fibrous layer 103 are joined to each other with adhesive applied to the entire periphery of each of the elastic members 104. The elastic sheet 100 has joining areas 107 in which the first and second fibrous layers 102,103 are joined to each other and non-joining areas 108 located between the joining areas 107.

In the elastic sheet 100, a spun-bonded fibrous nonwoven fabrics constructed of polypropylene fibers having a mass of 17.0 g/m² is used as the first fibrous layer 102, and a spun-bonded fibrous nonwoven fabric constructed of polypropylene fibers having a mass of 17.0 g/m² is used as the second fibrous layer 103. Terms and conditions including elastic materials for the elastic members 104, the fineness and pitch thereof are almost the same as the elastic members 4 disposed on the elastic sheet 10 according to one or more embodiments.

Referring to FIGS. 2 and 4, when compared to the elastic sheet 10 according to the present embodiment, the conventional elastic sheet 100 is formed with gathers-like concave and convex parts 120, 130 that are approximately uniform in size and relatively large in thickness (depth), and the number of the gathers of the elastic members 100 is less than the number of the gathers of the elastic members 10. This would be because the elastic sheet 10 has a relatively low flexural rigidity value, more specifically, each average value of the flexural rigidity value B1 of the first fibrous layer 2 and the flexural rigidity value B2 of the second fibrous layer 3 is $0.022 \times 10^{-4}$ (N·m²/m) or less, and thus the elastic sheet 10 has a configuration in which the ups and downs are repeated in the second direction X under the contractible force of the elastic members 4, shapes of the gathers are collapsed, and a plurality of small gathers that have non-uniform and relatively small thicknesses are formed.

[Measurement for Number of Gathers]

The number of the gathers of the elastic sheet 10 was determined by visually calculating the number of the convex parts 20 or the concave parts 30 in the range of a 50 mm length in the first direction Y×a pitch of the elastic member 4 from the side of the first surface 11 or the second surface 12 and by averaging (N=2) the number of the gathers. The number of the gathers of the conventional elastic sheet 100 described hereinafter was also calculated in the same way.

As described above, in the case where the thickness of the convex parts 120 is relatively large and uniform gathers are configured as the conventional elastic sheet 100, the aesthetic appearance is excellent, but the rigidity is high compared to the elastic sheet 10 having non-uniform gather structure with small thickness, and the gather marks may be left on a wearer's skin due to the convex parts 120 being bit deeply into the wearer's skin even when they are compressed during wearing. On the other hand, since the non-joining areas 8 of the elastic sheet 10 according to one or more embodiments have a plurality of non-uniform gathers having a low uneven degree, and thus the first surface 11 has high smoothness and has a relatively large contact area with the first surface 11 and the wearer's skin. Thus, when the wearer's skin comes in contact with the first surface 11 of the elastic sheet 10, the contact pressure exerted to the wearer's skin under the contractile force of the elastic members 4 is dispersed and the elastic sheet 10 may not bite into the wearer's skin, and thus the gather marks due to the convex parts 20 are unlikely to be left on the wearer's skin.

The thickness TO of each test piece under a micro load of the convex parts 20 of the elastic sheet 10, i.e., 0.49 hpa load in accordance with a KES method, is 2.70 to 4.70 mm, and the thickness Tm under 49.03 hpa load is 0.22 to 1.5 mm.

Under a predetermined load, the thickness Tm of the convex parts 20 of the elastic sheet 10 is less than 1.5 mm, which is relatively small, and each average value of the flexural rigidity values B1, B2 of the first and second fibrous layers 2, 3 is less than $0.022 \times 10^{-4}$ (N·m$^2$/m), and thus the gather shapes of the elastic sheet 10 are easily deformed by an external force.

The compression workload WC of the convex parts 20 of the elastic sheet 10 in accordance with the KES method is 0.236 to 5.0 N·m/m$^2$, and the compression resilience rate RC is 19 to 36%. Both the compression workload WC and the compression resilience rate RC are a relatively low numeric value, and the convex parts 20 are easily compressed by an external force and low in resilience after compressed. Thus, the convex parts 20 are easily compressed when come in contact with the wearer's skin, and since shape resilience properties after compressed are low, the repulsive force against the skin is low. Thus, the gather marks on the wearer's skin may be suppressed with the dispersion of the contact pressure.

As used herein, the term "good flexibility" of the first and second fibrous layers 2, 3 of the elastic sheet 10 means that the elastic sheet 10 has weak rigidity and low resilience at a degree such as the gathers are collapsed and only the shallow gather marks are left on the wearer's skin in a contact with the wearer's skin, unlike elastically contractible fibrous nonwoven fabrics including elastic fibers or other fibrous nonwoven fabrics, which are rich in elasticity.

For example, to improve the fittability to the wearer's skin, in the case where a pitch between the elastic members 4 is made small, the gather marks are easily left on the wearer's skin due to the stronger tightening force. However, the elastic sheet 10 having the flexibility and compression properties in accordance with the KES method makes it possible to suppress the gather marks from being left on the skin without forming of the gathers having relatively high concavity and convexity degree. Furthermore, in the case where an amount of hot melt adhesive applied to the entire peripheral of the elastic members 4 is increased to improve the adhesive properties to the first and second fibrous layers 2, 3 of the elastic members 4, the elastic sheet 10 is high in rigidity and the rubber elasticity marks are easily left on the skin. However, since the first fibrous layer 2 has good flexibility, the rigidity is not overly high, and makes it possible to suppress the rubber elasticity marks from being left on the skin.

With regard to each mechanical measurement in this description in accordance with the KES method, the details are described in "Standardization and analysis of texture valuation", Second Edition (an Incorporated Foundation—the Japan Textile Machinery Association, the Texture weighting and Normalized Research Council, issued on Jul. 10, 1980).

<Measurement Method for Thicknesses of Sheets TO, Tm and Compression Properties>

To measure thicknesses of sheets, Compression Testing Machine (KES-FB3-AUTO-A type) of Kato Tech Co., Ltd. in Japan was used. First, each test piece was cut out from the elastic sheet 10 in a size of 10.0 cm×10.0 cm and was fixed on a test stand of metal plane in a contracted state so that the second fibrous layer was on the lower surface side of the test stand and the first fibrous layer was on the upper surface side thereof (measuring surface side). The center of each test piece was quietly sandwiched between both disks each having a compression area of about 2.0 cm$^2$ (an area of each desk), located on the upper and lower sides, and a thickness TO of each test piece was measured under a load of 0.49 pha. Next, the thickness Tm of each test piece was measured by compressing them up to being a load of 49.03 hpa at an acceleration rate of 50 mm/second. Also, a compression resilience rate RC (%) was obtained in accordance with the following formula, wherein a workload [N·m/m$^2$] required at the time when compressing from the thickness TO to the thickness Tm was set as WC, and a workload required at the time when recovering from the thickness Tm to the thickness TO is set as WC2.

$$RC(\%)=WC2/WC \times 100$$

In the elastic sheet 10 according to one or more embodiments, the first fibrous layer 2 is formed of a spun-bonded nonwoven fabric including polyethylene fibers and the second fibrous layer 3 is formed of a spun-bonded fibrous nonwoven fabric including polypropylene fibers, however, both the first and second fibrous layers 2, 3 may be formed of the spun-bonded fibrous nonwoven fabric including the polyethylene fibers. In such case, since the first and second fibrous layers 2, 3 are excellent in flexibility, their average flexural rigidity value and thickness Tm under a load are equal to or less than those of the elastic sheet 10 in the present embodiment. Since both the first and second fibrous layers 2, 3 are formed of a flexible fibrous nonwoven fabric, they would be formed with small gathers having a low degree of concavity and convexity compared to the elastic sheet 10 according to the present embodiment.

Table 1 shows evaluations for properties and performance of a plurality of elastic sheets manufactured under various conditions in order to compare to the conventional products. Elastic sheets according to examples 1 to 6 and comparison examples 1 to 3 are composite sheets, which were composed of first and second fibrous sheets and elastic members interposed therebetween, and the first and second fibrous layers were joined to each other with hot melt adhesive of a mass of 0.07 g/m$^2$ applied to the entire periphery of the elastic members.

TABLE 1

|  | Example 1 | Example 2 | Example 3 | Example 4 | Example 5 | Example 6 | Comparison Example 1 | Comparison Example 2 | Comparison Example 3 |
|---|---|---|---|---|---|---|---|---|---|
| Flexural rigidity value $10^{-4}$ (N · m²/m) | 0.0215 | 0.0044 | 0.0215 | 0.0044 | 0.0081 | 0.0065 | 0.0386 | 0.0386 | 0.0386 |
| Compression workload WC (N * m/m²) | 4.51 | 2.49 | 4.88 | 2.63 | 2.81 | 2.38 | 6.93 | 5.47 | 2.76 |
| Compression resilience rate RC (%) | 29.04 | 19.63 | 32.27 | 29.59 | 35.56 | 30.77 | 25.22 | 33.21 | 36.99 |
| Initial thickness T0 (mm) | 4.64 | 3.71 | 4.73 | 3.23 | 2.98 | 2.72 | 6.74 | 5.04 | 3.59 |
| Thickness under load Tm (mm) | 1.4 | 0.8 | 1.41 | 0.83 | 1.37 | 1.15 | 1.75 | 1.98 | 2.00 |
| Number of gathers (piece/50 mm length) | 14 | 15 | 14 | 18 | 17 | 22 | 7 | 10 | 15 |
| Evaluation results of gather level | 1.7 | 1 | 2 | 1 | 3 | 2 | 3.7 | 4.3 | 4.7 |

Example 1

As the first fibrous layer 2, a spun-bonded fibrous nonwoven fabric constructed of polyethylene fibers having a mass of 17.0 g/m², and as the second fibrous layer 3, a spun-bonded fibrous nonwoven fabric constructed of polypropylene fibers having a mass of 17.0 g/m², were respectively used. As a plurality of elastic members, polyurethane threads having a fineness of 470 dtex were used, and the elastic members were contractibly secured between the first and second fibrous layers in a state stretched by 2.5 times under a pitch of 9.0 mm.

Example 2

As the first fibrous layer 2, a spun-bonded fibrous nonwoven fabric constructed of polyethylene fibers having a mass of 17.0 g/m², and as the second fibrous layer 3, a spun-bonded fibrous nonwoven fabric constructed of polyethylene fibers having a mass of 17.0 g/m², were respectively used. As a plurality of elastic members, polyurethane threads having a fineness of 470 dtex were used, and the elastic members were contractibly secured between the first and second fibrous layers in a state stretched by 2.5 times under a pitch of 9.0 mm.

Example 3

As the first fibrous layer 2, a spun-bonded fibrous nonwoven fabric constructed of polyethylene fibers having a mass of 17.0 g/m², and as the second fibrous layer 3, a spun-bonded fibrous nonwoven fabric constructed of polypropylene fibers having a mass of 17.0 g/m², were respectively used. As a plurality of elastic members 4, polyurethane threads having a fineness of 940 dtex were used, and the elastic members were contractibly secured between the first and second fibrous layers in a state stretched by 2.5 times under a pitch of 9.0 mm.

Example 4

As the first fibrous layer 2, a spun-bonded fibrous nonwoven fabric constructed of polyethylene fibers having a mass of 17.0 g/m², and as the second fibrous layer 3, a spun-bonded fibrous nonwoven fabric constructed of polyethylene fibers having a mass of 17.0 g/m², were respectively used. As a plurality of elastic members 4, polyurethane threads having fineness of 940 dtex were used, and the elastic members were contractibly secured between the first and second fibrous layers in a state stretched by 2.5 times under a pitch of 9.0 mm Example 5

As the first fibrous layer 2, a spun-bonded fibrous nonwoven fabric constructed of polyethylene fibers having a mass of 25.0 g/m², and as the second fibrous layer 3, a spun-bonded fibrous nonwoven fabric constructed of polypropylene fibers having a mass of 14.0 g/m², were respectively used. As a plurality of elastic members 4, polyurethane threads having a fineness of 470 dtex was used, and the elastic members were contractibly secured between the first and second fibrous layers in a state stretched by 2.5 times under a pitch of 5.0 mm.

Example 6

As the first fibrous layer 2, a spun-bonded fibrous nonwoven fabric constructed of polyethylene fibers having a mass of 20.0 g/m², and as the second fibrous layer 3, a spun-bonded fibrous nonwoven fabric constructed of polyethylene fibers having a mass of 20.0 g/m², were respectively used. As a plurality of elastic members 4, polyurethane threads having fineness of 470 dtex were used, and the elastic members were contractibly secured between the first and second fibrous layers in a state stretched by 2.5 times under a pitch of 5.0 mm.

Comparison Example 1

As the first fibrous layer 2, a spun-bonded fibrous nonwoven fabric constructed of polypropylene fibers having a mass of 17.0 g/m², and as the second fibrous layer 3, a spun-bonded fibrous nonwoven fabric constructed of polypropylene fibers having a mass of 17.0 g/m², were respectively used. As elastic members, polyurethane threads having fineness of 470 dtex were used, and the elastic members were contractibly secured between the first and second fibrous layers in a state stretched by 2.5 times under a pitch of 9.0 mm.

Comparison Example 2

As the first fibrous layer 2, a spun-bonded fibrous nonwoven fabric constructed of polypropylene fibers having a mass of 17.0 g/m², and as the second fibrous layer 3, a spun-bonded fibrous nonwoven fabric constructed of polypropylene fibers having a mass of 17.0 g/m², were respectively used. As elastic members, polyurethane threads having a fineness of 940 dtex were used, and the elastic members were contractibly secured between the first and second fibrous layers in a state stretched by 2.5 times under a pitch of 9.0 mm.

Comparison Example 3

As the first fibrous layer 2, a spun-bonded fibrous nonwoven fabric constructed of polypropylene fibers having a mass of 17.0 g/m², and as the second fibrous layer, a spun-bonded fibrous nonwoven fabric constructed of polypropylene fibers having a mass of 17.0 g/m², were respectively used. As a plurality of elastic members, polyurethane threads having a fineness of 470 dtex was used, and the elastic members were contractibly secured between the first and second fibrous layers in a state stretched by 2.5 times under a pitch of 5.0 mm.

The flexural rigidity value, the compression workload WC, the compression resilience rate RC, the initial thickness TO, the thickness Tm under a load, and the number of gathers were measured in accordance with the above measuring method. The evaluation results of the gather marks level were obtained by the following evaluation method.

[Evaluation Method of Gather Marks Level]

First, the elastic sheet for each example and each comparison example were cut in sizes of length 180 mm×width 100 mm. Next, each annular test piece of circumference 140 cm was formed by connecting both ends of each cut sheet. Then, each annular test piece was put on the forearms of search participants for 30 minutes, and after removed, the level of the gather marks left on the forearm was determined by visual observation. This measurement was carried out to 10 search participants (5 adult males, 5 adult females). The average value of the level of the gather marks left on the forearms of 10 search participants was regarded as each gather mark level in each example and each comparison example.

Levels 1 to 5 of the gather marks respectively mean the following states:

Level 1: no gathers, a state that only a rubber elasticity mark was visually recognized;

Level 2: a state that the gather marks extending longitudinally from rubber elasticity marks were visually recognized;

Level 3: a state that the gather marks were more prominent than the rubber elasticity marks, and multiple gather marks extending longitudinally in about 1 to 3 mm from the rubber elasticity marks were visually recognized;

Level 4: a state that, in addition to the gather marks recognized in Level 3, the gather marks were visually recognized extending longitudinally in 5 mm or more between the elastic members; and Level 5: a state that the gather marks extending longitudinally in 5 mm or more, recognized in Level 4, were recognized in 10 or more in a predetermined range (200 mm×50 mm).

[Measurement Results]

As shown in Table 1, the thickness Tm under a load of the elastic sheet 10 according to examples 1 to 6 was 1.5 mm or less, an average flexural rigidity value of the first and second fibrous layers was $0.022 \times 10^{-4}$ (N·m²/m) or less, and the gather marks level was 3 or less. On the other hand, thickness Tm under a load of the elastic sheet according to comparison examples 1 to 3 was 1.5 mm or more, an average flexural rigidity value of the first and second fibrous layers was 0.03 or more, and the gather marks level was 3 or more. In view of the above, when in the elastic sheet, the thickness Tm under the load and the average flexural rigidity value of the first and second fibrous layers are large, it can be said that the gather marks level tend to be higher.

In a comparison between example 1 and example 3, when the fineness of the elastic members 4 is large, the gather mark level is also relatively large, but the gather marks level is maintained to the degree that there are no gather marks left more prominent than the rubber elasticity gather marks. In a comparison between example 1 and example 5, when the mass of the first fibrous layer 3 is higher and the pitch between the elastic members 4 is smaller, the gather marks level is higher, but even in such case, the level is maintained to the degree that the longitudinal gather marks by 5 mm or more are not left at least between the elastic members 4. In this way, even the case where the fineness of the elastic members 4 is relatively large and the pitch between the elastic members 4 is relatively large, the rigidity of the elastic sheet 10 itself is low and the large gather marks are not left on the wearer's skin because the gathers do not collapse and the wearer's skin is not strongly compressed.

Figure 6:
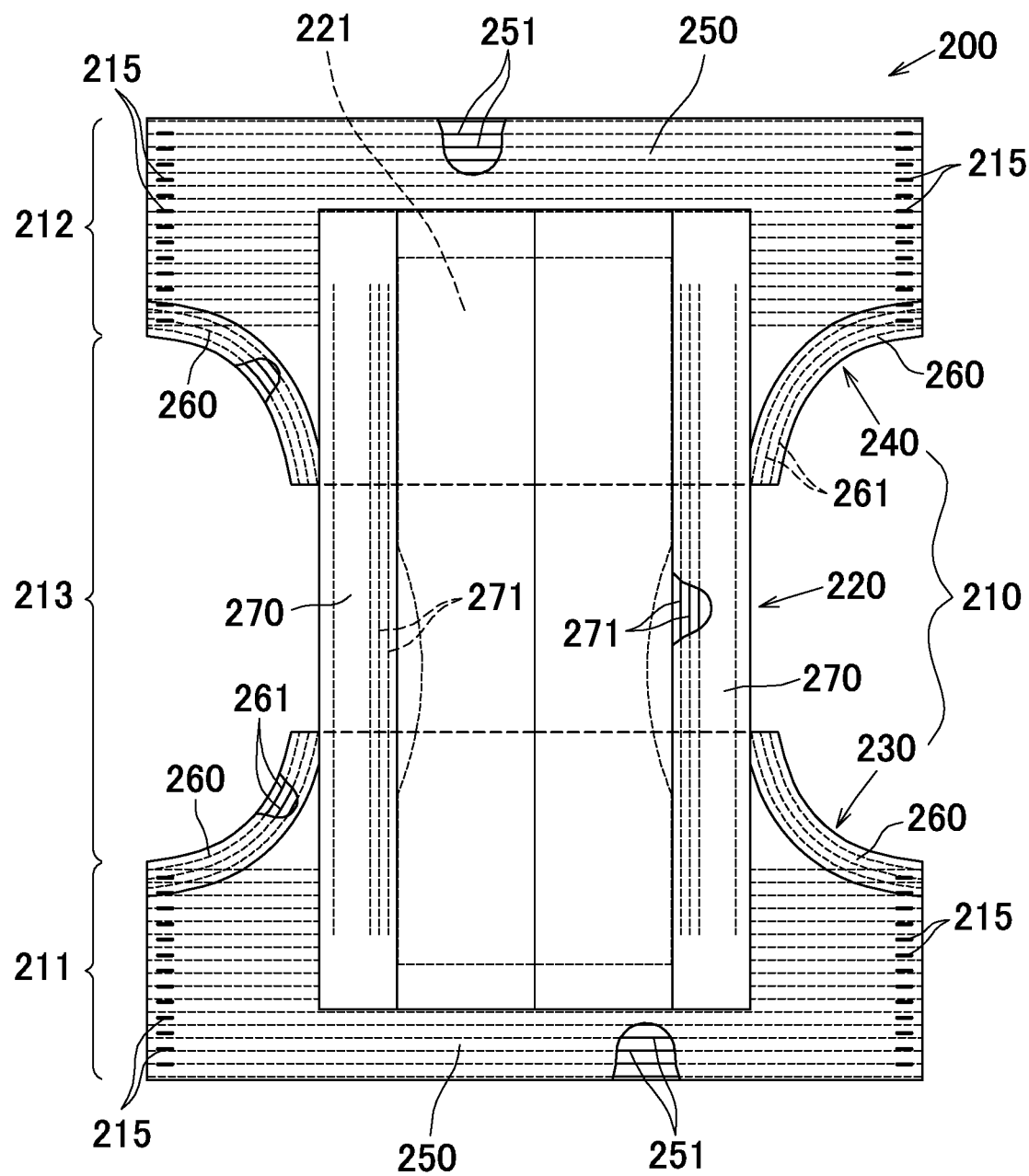
FIG. 6 is a partial cutaway opened plan view of a disposable diaper as an example of a disposable article, viewed from the inside of the diaper at the maximum extension of elastic members secured thereto in the longitudinal and transverse directions (to an extent that gathers formed by the elastic members disappear).

FIG. 6 shows a partially cutaway opened view from the inside of a disposable diaper 200 as an example of absorbent article, using the elastic sheet according to one or more embodiments, and at the when stretched longitudinally and transversely up to the maximum extension of each elastic member (to the degree that the gathers by the contraction of the elastic materials disappear).

Referring to FIG. 6, a diaper 200 has a longitudinal direction P and transverse direction Q intersecting with the direction P, and include an elastic waist panel 210 extending annularly to a waist circumference direction, an absorbent panel 220 attached onto the inside of the elastic waist panel 210, a front waist region 211, a rear waist region 212, and a crotch region 213 extending between the front and rear waist regions 211,212. The elastic waist panel 210 is constructed of a front waist panel 230 defining the front waist region 211 and a rear waist panel 240 defining the rear waist region 212. Both side edges of the front waist panel 230 and both side edges of the rear waist panel 240 are overlapped with each other and connected to each other by side seams 215 arranged continually in the longitudinal direction Y to define a waist opening and a pair of leg openings.

The front and rear waist panels 230, 240 are formed of waist elastic sheets 250 arranged with a plurality of elastic members 251 extending in the transverse direction Q, and in the leg opening edges, there are disposed leg elastic sheets 260 having a plurality of leg elastic members 261 extending in the peripheral of the leg openings. The absorbent panel 220 includes an absorbent structure 221 having an absorbability of body fluids and a pair of leakage barrier flaps 270 extending in the longitudinal direction Y on both sides in the transverse direction X of the absorbent structure. The leakage barrier flaps 270 have a plurality of flap elastic members 271 extending in the longitudinal direction Y attached to free edges thereof.

The diaper 200 is disposed with an elastic sheet 10 as at least one of the waist elastic sheets 250, leg elastic sheets 260 and the leakage barrier flaps 270. When the elastic sheet 10 is used as at least one of those sheets and flaps 250, 260 and 270, the waist elastic members 251, leg elastic members 261 and flap elastic members 271 respectively correspond to the elastic members 4 of the elastic sheet 10. In such case, the first surface 11 of the elastic sheet 10 may be located on the skin facing surface side of the wearer and the second surface 12 of the elastic sheet 10 is located on the non-skin facing surface side opposed thereto.

In the case where the elastic sheet 10 is used as the waist elastic sheet 250, even when the waist elastic members 251 have tensile stresses to the degree that the front and rear waist regions 211, 212 exert the required holding force, the contact of the first surface 11 of the elastic sheet 10 with a wearer's skin does not make the waist opening edge bit into the skin with dispersion of the contact pressure generated by contractile force of the waist elastic members 251, and thus the gather marks are unlikely to be left on the skin. A similar effect is exhibited even when the elastic sheet 10 is used as the leg elastic sheet 260 and the leakage barrier flap 270. In particular, since these sheets 260, 270 are brought in contact with the thighs and the groins, which are more sensitive than the waist parts of the wearer, the gather marks are easily left on the wearer's skin. However, the use of the elastic sheet 10 makes it possible to suppress the gather marks from being deeply left.

The terms "first" and "second" in the description and the claims are used for distinguishing between similar elements and not necessary for describing a sequential or chronological order. It is to be understood that the terms so used are interchangeable under appropriate circumstances and that embodiments described herein are capable of operation in other sequences than described or illustrated herein. It is to be noticed that the term "comprising" used in the claim should not be interpreted as being restricted to the means listed thereafter; it does not exclude other elements or step.

Although the disclosure has been described with respect to only a limited number of embodiments, those skilled in the art, having benefit of this disclosure, will appreciate that various other embodiments may be devised without departing from the scope of the present invention. Accordingly, the scope of the invention should be limited only by the attached claims.

2 first fibrous layer
3 second fibrous layer
4 elastic members
10 elastic sheet
11 first surface (skin facing surface)
12 second surface (non-skin facing surface)
20 convex part
30 concave part
200 absorbent article
211 front waist region
212 rear waist region
213 crotch region
250 waist elastic sheet
260 leg elastic sheet
270 leakage barrier flap

What is claimed is:

1. The elastic sheet for an absorbent article comprising:
a first fibrous layer comprising a first surface of the elastic sheet;
a second fibrous layer comprising a second surface of the elastic sheet opposite the first surface; and
contractible elastic members extending in a first direction and secured between the first fibrous layer and the second fibrous layer, the first fibrous layer and the second fibrous layer having a plurality of gathers disposed in a second direction intersecting the first direction and also formed between elastic members,
wherein the first fibrous layer comprises a spun-bonded or spun-melt nonwoven fabric including continuous polyethylene fibers and wherein a second fibrous layer comprises a spun-bonded or spun-melt nonwoven fabric including continuous polyethylene and/or polypropylene fibers,
an average flexural rigidity value of the first fibrous layer and second fibrous layer is $0.0035 \times 10^{-4}$ to $0.022 \times 10^{-4}$ $N \cdot m^2/m$ as measured according to a Kawabata Evaluation System (KES) method, and
a thickness of 0.22 to 1.5 mm under a compression load of 49.03 hPa to the gathers as measured according to a KES method.

2. The elastic sheet according to claim 1, comprising an initial thickness of 2.70 to 4.70 mm under a micro-load to the gathers of 0.49 hPa according to the KES method.

3. The elastic sheet according to claim 1, wherein
the gathers between adjacent elastic members are formed such that a convexity is formed as viewed from the first surface and a concavity is formed as viewed from the second surface.

4. The elastic sheet according to claim 1, wherein
a compression workload under the compression load to the gathers is 0.236 to 5.0 $N \cdot m/m^2$, and
a compression resilience rate under the compression load to the gathers is 19 to 36%.

5. The elastic sheet according to claim 1, wherein
the first fibrous layer and the second fibrous layer each comprise fused parts, where the continuous fibers are fused, and non-fused parts, wherein a rigidity difference between the fusion parts and non-fused parts in the second fibrous layer is larger than a rigidity difference between the fused parts and the non-fused parts.

6. The elastic sheet according to claim 1, wherein
a basis weight of each of the first fibrous layer and the second fibrous layer is 10 to 30 $g/m^2$,
a density of each of the first fibrous layer and the second fibrous layer is 0.04 to 0.15 $g/m^3$, and
a pitch between the elastic members in the intersecting direction is 2.0 to 12.0 mm.

7. The elastic sheet according to claim 1, wherein a fineness of the polyethylene fibers is 1.5 to 4.0 dtex and a fineness of the polypropylene fibers, if present, is 0.9 to 2.5 dtex.

8. An absorbent article comprising the elastic sheet according to claim 1, wherein
the first surface is a skin-facing surface, and
the second surface is a non-skin facing surface opposite to the skin facing surface.

9. The absorbent article according to claim 8, wherein
the absorbent article is a disposable diaper having a front waist region, a rear waist region, and a crotch region, wherein
the elastic sheet forms one or more of a waist elastic sheet forming the front and rear waist regions, a leg elastic sheet disposed along a leg opening edge in the crotch region, and a leakage barrier flap extending from the crotch region to the front and rear waist regions.

10. The elastic sheet for an absorbent article comprising:
a first fibrous layer comprising a first surface of the elastic sheet;
a second fibrous layer comprising a second surface of the elastic sheet opposite the first surface; and
contractible elastic members extending in a first direction and secured between the first fibrous layer and the second fibrous layer, the first fibrous layer and the second fibrous layer having a plurality of gathers disposed in a second direction intersecting the first direction and also formed such that a convexity is formed as viewed from the first surface and a concavity is formed as viewed from the second surface between adjacent elastic members, wherein the first fibrous layer and the second fibrous layer comprise a spun-bonded or spun-melt nonwoven fabric including continuous thermoplastic fibers;

an average flexural rigidity value of the first fibrous layer and second fibrous layer is $0.0035 \times 10^{-4}$ to $0.022 \times 10^{-4}$ N·m$^2$/m as measured according to a Kawabata Evaluation System (KES) method, and a thickness under a compression load of 49.03 hPa to the gathers is 0.22 to 1.5 mm as measured according to a KES method.

11. The elastic sheet according to claim 10, comprising an initial thickness of 2.70 to 4.70 mm under a micro-load to the gathers of 0.49 hPa according to the KES method.

12. The elastic sheet according to claim 10, wherein the thermoplastic fibers are polyethylene fibers for the first fibrous layer and wherein the thermoplastic fibers are polyethylene and/or polypropylene fibers for the second fibrous layer.

13. The elastic sheet according to claim 10, wherein a compression workload under the compression load to the gathers is 0.236 to 5.0 N·m/m$^2$, and a compression resilience rate under the compression load to the gathers is 19 to 36%.

14. The elastic sheet according to claim 10, wherein the first fibrous layer and the second fibrous layer each comprise fused parts, where the continuous fibers are fused, and non-fused parts, wherein a rigidity difference between the fusion parts and non-fused parts in the second fibrous layer is larger than a rigidity difference between the fused parts and the non-fused parts.

15. The elastic sheet according to claim 10, wherein a basis weight of each of the first fibrous layer and the second fibrous layer is 10 to 30 g/m$^2$, a density of each of the first fibrous layer and the second fibrous layer is 0.04 to 0.15 g/m$^3$, and a pitch between the elastic members in the intersecting direction is 2.0 to 12.0 mm.

16. The elastic sheet according to claim 12, wherein a fineness of the polyethylene fibers is 1.5 to 4.0 dtex and a fineness of the polypropylene fibers, if present, is 0.9 to 2.5 dtex.

17. An absorbent article comprising the elastic sheet according to claim 10, wherein the first surface is a skin-facing surface, and the second surface is a non-skin facing surface opposite to the skin facing surface.

18. The absorbent article according to claim 17, wherein the absorbent article is a disposable diaper having a front waist region, a rear waist region, and a crotch region, wherein the elastic sheet forms one or more of a waist elastic sheet forming the front and rear waist regions, a leg elastic sheet disposed along a leg opening edge in the crotch region, and a leakage barrier flap extending from the crotch region to the front and rear waist regions.

19. The elastic sheet for an absorbent article comprising:

a first fibrous layer comprising a first surface of the elastic sheet;

a second fibrous layer comprising a second surface of the elastic sheet opposite the first surface; and contractible elastic members extending in a first direction and secured between the first fibrous layer and the second fibrous layer, the first fibrous layer and the second fibrous layer having a plurality of gathers disposed in a second direction intersecting the first direction and also formed between elastic members, wherein the first fibrous layer and the second fibrous layer comprise a spun-bonded or spun-melt nonwoven fabric including continuous thermoplastic fibers, wherein the thermoplastic fibers comprise polyethylene fibers in at least one of the first fibrous layer and the second fibrous layer;

an average flexural rigidity value of the first fibrous layer and second fibrous layer is $0.0035 \times 10^{-4}$ to $0.022 \times 10^{-4}$ N·m$^2$/m as measured according to a Kawabata Evaluation System (KES) method, and a thickness of 2.70 to 4.70 mm under a micro-load of 0.49 hPa to the gathers and a thickness of 0.22 to 1.5 mm under a compression load of 49.03 hPa to the gathers as measured according to a KES method.

20. An absorbent article comprising the elastic sheet according to claim 19, wherein the first surface is a skin-facing surface, and the second surface is a non-skin facing surface opposite to the skin facing surface.

* * * * *